United States Patent [19]

Ford et al.

[11] 4,399,308

[45] Aug. 16, 1983

[54] LEWIS ACID HALIDE CATALYSTS FOR PREPARATION OF POLYAMINES

[75] Inventors: Michael E. Ford, Trexlertown; Thomas A. Johnson, Orefield, both of Pa.

[73] Assignee: Air Products and Chemicals, Inc., Allentown, Pa.

[21] Appl. No.: 258,251

[22] Filed: Apr. 28, 1981

[51] Int. Cl.$^3$ .............................................. C07C 85/06
[52] U.S. Cl. ................................... 564/479; 564/480; 564/511; 564/512
[58] Field of Search ................................ 564/479, 480

[56] References Cited

U.S. PATENT DOCUMENTS

| 2,000,410 | 5/1935 | Morrell et al. | 564/402 X |
| 2,085,785 | 7/1937 | Bottoms | 564/480 |
| 3,708,539 | 1/1973 | Fenton | 564/480 |
| 3,714,259 | 1/1973 | Lichtenwalter et al. | 564/479 |
| 3,751,474 | 8/1973 | Phillips et al. | 564/479 |
| 3,755,447 | 8/1973 | Klemann et al. | 564/479 |
| 4,036,881 | 7/1977 | Brennan et al. | 564/479 |
| 4,044,053 | 8/1977 | Brennan et al. | 564/479 |

FOREIGN PATENT DOCUMENTS 1542359 11/1967 France .............................. 564/479

*Primary Examiner*—John Doll
*Attorney, Agent, or Firm*—Michael Leach; E. Eugene Innis; James C. Simmons

[57] ABSTRACT

A process for selectively preparing predominantly non-cyclic polyalkylene polyamine compounds is disclosed wherein an alkylene polyamine compound is contacted with an alkanolamine compound in the presence of a catalytically effective amount of a Lewis acid halide substance at a temperature of from 200° to 350° C. under a pressure sufficient to maintain the reaction mixture essentially in liquid phase. The polyalkylene polyamine thus formed is recovered from the reaction mixture.

10 Claims, No Drawings

LEWIS ACID HALIDE CATALYSTS FOR PREPARATION OF POLYAMINES

TECHNICAL FIELD

This invention relates to the preparation of polyalkylene polyamines. More particularly, it relates to the preparation of linear and branched, or non-cyclic, polyalkylene polyamines.

BACKGROUND OF PRIOR ART

One of the early techniques for preparing linear polyalkylene polyamine compounds, such as diethylenetriamine and triethylenetetramine and higher homologues, has been to react an alkyl halide with an amine such as ammonia, ethylenediamine and the like at elevated temperatures and pressures. Generally, high yields of cyclic polyethylene polyamines, e.g. piperazine, triethylenediamine as well as other cyclic amines were produced. Another problem in the process was that hydrohalide salts of ammonia or hydrogen chloride were produced by the reaction, and thus expensive corrosion resistant equipment was required. U.S. Pat. No. 3,751,474 is representative.

More recently, a series of patents disclosed the preparation of linear polyalkylene polyamine compounds by reacting a diol or an alkanolamine compound with an alkylenediamine compound under preselected process conditions. These include:

U.S. Pat. No. 3,714,259, which shows preparing linear poly(ethylene)amines by contacting ethanolamine with an ethylenediamine compound in the presence of hydrogen and hydrogenation catalyst. An example of a hydrogenation catalyst in nickel containing copper and chromium components;

U.S. Pat. No. 4,036,881, which shows the preparation of polyalkylene polyamines by reacting an alkanolamine with an alkyleneamine compound in the presence of a phosphorous-containing substance selected from the group consisting of acidic metal phosphates, phosphoric acid compounds and hydrides and phosphate esters; and U.S. Pat. No. 4,044,053, which is somewhat similar to the '881 patent except that the alkyleneamine compound is present in an excess amount and a diol is used in place of the alkanolamine.

In French Pat. No. 1,542,359 a process is disclosed for the preparation of poly(ethylene)amines by the polymerization of ethanolamine in the presence of carbon dioxide and a strong base such as potassium carbonate or sodium hydroxide. The products of this process are high polymers of a waxy nature.

SUMMARY OF THE INVENTION

It has been found that non-cyclic, or linear and branched, polyalkylene polyamines are produced in good yield with good selectivity directly by reacting an alkyleneamine compound and an alkanolamine compound in the presence of an effective amount of a Lewis acid halide substance at a temperature sufficient to effect reaction between the alkyleneamine and the alkanolamine compounds under a pressure sufficient to maintain the reaction mixture essentially in liquid phase.

DETAILED DESCRIPTION OF THE INVENTION

Briefly, the invention relates to a process for synthesizing predominantly non-cyclic polyalkylene polyamines, and preferably predominantly linear and branched polyethylene polyamines such as diethylenetriamine and higher homologues. In the process an alkyleneamine having two primary amino groups and, preferably, an unbranched alkylene moiety, such as ethylenediamine, is reacted with an alkanolamine having a primary or secondary hydroxy moiety and a primary amine group. Preferably, the alkanolamine has an unbranched alkylene moiety.

The alkyleneamine reactants that can be used in practicing the process are represented by the general formula:

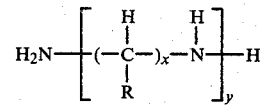

where R is a hydrogen or a lower alkyl ($C_1$–$C_4$) radical, x is a number from 2 to about 6, and y is a number from 1 to about 4. The preferred lower alkyl radical is methyl. Examples of alkylenediamine compounds suited for the reaction include 1,3-propylenediamine, 1,2-propylenediamine, diethylenetriamine, triethylenetetramine and ethylenediamine which is the preferred alkylenediamine composition.

The alkanolamine compounds which are used in practicing the process include those represented by the general formula:

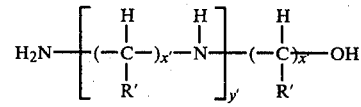

wherein R' is hydrogen or a lower alkyl ($C_1$–$C_4$) radical; X' is a number from 2 to about 6; and y' is a number from 0 to 3. Methyl is the preferred lower alkyl radical. Examples of alkanolamine compounds that can be used are ethanolamine, isomeric propanolamines, N-(2-aminoethyl)ethanolamine.

Linear polyalkylene polyamines that are produced by the reaction of an alkylenediamine and an alkanolamine may be represented by the general formula:

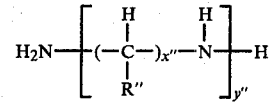

wherein R" is hydrogen or a lower alkyl ($C_1$–$C_4$) radical, preferably a methyl radical; X" is a number from 2 to about 6; y" is a number from 2 to about 7; and x" may vary for a given value of y". Examples of linear polyalkylene polyamines that are produced include di-propylenetriamine, tributylenetetramine, di-(2-methylethylene)triamine, tri-(2-methylethylene)tetramine, N-(2-aminoethyl)-1,3-propylenediamine, diethylenetriamine, triethylenetetramine and tetraethylenepentamine.

The catalysts which are suited for practicing the process described herein are Lewis acid halide substances. The catalyst is a halide salt, preferably, a fluoride, chloride or bromide salt, of a Lewis acid metal. Virtually any Lewis acid metal can be used, and these generally include the metals of Groups I-B, II-A, II-B, III-A, IV-A and the first row of Group VIII of the Periodic Table. Representative Lewis acid metals are copper, silver, beryllium, magnesium, zinc, cadmium, boron, aluminum, tin, iron, cobalt and nickel. The preferred Lewis acid metals are aluminum, tin, zinc, cobalt and magnesium.

A Lewis acid is a substance that can take up an electron pair to form a covalent bond-an electron pair acceptor. Lewis acids include compounds having less than a full octet of electrons, such as boron trifluoride; positive ions, particularly polyvalent ions which are strongly hydrated in aqueous solution; compounds having double bonds excepting carbon-carbon double bonds; and metal halide compounds in which the central atom may exceed its octet, such as stannic chloride, titanium tetrabromide and molecular iodine. The Lewis acid halide catalysts used in the process of this invention for preparing predominantly linear polyalkylene polyamines comprise this latter category. Further examples of such Lewis acid halides useful as catalysts include aluminum chloride, tin (IV) chloride, zinc fluoride, cobalt fluoride, zinc chloride, magnesium chloride, beryllium chloride and iron (III) chloride. Other examples are aluminum bromide, zinc bromide, magnesium fluoride, and magnesium bromide.

The above-mentioned Lewis acid halide substances are not intended to be exhaustive of those which may be employed as a catalyst material. However, as might be expected, it is preferred to use those which are more reactive and provide for substantial conversion with high selectivity to the desired product.

The quantity of Lewis acid halide substance used in the reaction is somewhat empirical and can vary widely depending upon the reactivity of the catalyst and the reactivity of the reactants present. An effective amount of a Lewis acid halide substance is used; in other words, an amount which causes a reaction between the alkylenediamine and the alkanolamine to yield linear or branched polyalkylene polyamine products at the temperature and pressure used. Usually, though, the amount used to provide a catalytic effect ranges from about 0.01 to 10.0 mole percent based upon the total amount of the alkylenediamine compound and alkanolamine feed present in the reaction mixture, and preferably in an amount of from about 0.05 to 5.0 mole percent. It is most preferred that levels of catalyst incorporation range from 0.3 to 2.5 mole percent based on the total amount of alkylenediamine and alkanolamine compounds. Within these ranges though, the level of catalyst again is somewhat empirical and is adjusted depending on the product state desired. Generally, it has been found that as the level of the catalyst increases and conversion increases, selectivity is somewhat reduced. Therefore, in those instances where there is substantial catalytic activity, the quantity of catalyst may be reduced to increase selectivity with a concomitant reduction in conversion.

In the preparation of linear polyalkylene polyamines, and preferably the linear polyethylene polyamines, the reaction is maintained at a temperature of from about 200° C. to about 350° C., and preferably from about 250° to 300° C. The pressure utilized for carrying out the reaction is that autogenous pressure which is sufficient to maintain the reaction in essentially liquid phase. When utilizing these temperatures and pressures, the reaction is allowed to proceed until a desired conversion is obtained or reaction is complete. Normally the reaction is carried out within about 0.1 to 4 hours.

Generally, the mole ratio of alkylenediamine compound to alkanolamine compound may range from about 1:10 to 10:1, and preferably ranges from about 1:5 to 5:1. It is advantageous in carrying out the process that the proportion of alkylenediamine compound to alkanolamine compound be in a stoichiometric excess, e.g. up to 10:1, to result in highest selectivity to linear product. When the alkylenediamine compound approaches a 1:1 molar ratio with the alkanolamine, or falls below that level, the alkanolamine may have a tendency to form the cyclic amine compositions. Accordingly, the most preferred molar ratio range of alkylenediamine compound to alkanolamine compound is from about 1:1 to 3:1.

Recovery of the linear polyalkylene polyamines from the reaction mixture can be accomplished by conventional techniques, these techniques generally involving a distillation. Advantageously, a small amount of a salt, such as the one used as the catalytic material, is added to the polyalkylene polyamine separation purification as described in U.S. Pat. No. 3,755,447.

The following examples illustrate the nature of the process described herein and are not intended to limit the scope of the invention.

EXAMPLES 1-5

A series of runs 1-5 were made to produce linear polyethylene polyamines by the reaction of ethylenediamine and monoethanolamine in a mole ratio of 1:2 by weight in the presence of Lewis acid halide catalysts. The reaction was carried out in a two milliliter shaker reactor under autogenous pressure at a temperature of 300° C. Such pressure may be about 1000-1200 psig. Each reaction was carried out for about two hours. At the completion of the reaction, the contents were cooled and the reaction mixture analyzed by gas liquid chromatography.

Tables 1 and 2 show results in terms of the amount of polyamines produced by the reactions. Conversion and selectivity are specified. The catalytic component was varied on the basis of weight mole percent of the total feed of ethylenediamine and monoethanolamine as indicated and was evaluated on the basis of its performance.

EXAMPLE 6

This run, which attempted to duplicate the art in terms of the catalyst taught by U.S. Pat. No. 4,036,881 for comparative purposes, was performed according to the procedure of Example 1 of the disclosure with the inclusion of boron phosphate (33 mg; 5.0 mole percent, based on total amine feed) in place of aluminum chloride as catalyst for copolymerization of ethylenediamine and monoethanolamine which are present in a mole ratio of 1:2. Upon completion of the reaction, the contents of the reactor were cooled and the reaction mixture analyzed by gas liquid chromatography.

TABLE 1

| POLYETHYLENE AMINES FROM ETHYLENEDIAMINE AND MONOETHANOLAMINE[a] | | | | | | | | | |
|---|---|---|---|---|---|---|---|---|---|
| RUN | CATALYST | LEVEL MOLE % | TEMP. °C. | PIP | TEDA | DETA | AEP | TAEA | TETA |

TABLE 1-continued

POLYETHYLENE AMINES FROM ETHYLENEDIAMINE AND MONOETHANOLAMINE[a]

| | | | | | | | | | |
|---|---|---|---|---|---|---|---|---|---|
| 1 | Aluminum Chloride | 2.5 | 300 | 2.93 | 0.73 | 2.51 | 18.24 | 2.51 | 0.00 |
| 2 | Tin(IV) Chloride | 2.5 | 300 | 21.34 | 5.54 | 5.32 | 22.66 | 6.07 | 0.00 |
| 3 | Zinc Fluoride | 5.0 | 300 | 13.52 | 2.40 | 8.88 | 5.68 | 4.00 | 3.44 |
| 4 | Cobalt Fluoride | 5.0 | 300 | 20.65 | 2.25 | 6.45 | 11.20 | 0.75 | 0.70 |
| 5 | Zinc Chloride | 5.0 | 300 | 2.58 | 2.94 | 13.80 | 13.62 | 3.24 | 0.96 |

| RUN | CATALYST | LEVEL MOLE % | TEMP. °C. | BAEP | PEEDA | AE-TETA | TEPA | AE-BAEP | AE-PEEDA |
|---|---|---|---|---|---|---|---|---|---|
| 1 | Aluminum Chloride | 2.5 | 300 | 12.67 | 0.00 | 0.00 | 0.00 | 0.00 | 0.00 |
| 2 | Tin(IV) Chloride | 2.5 | 300 | 11.18 | 1.14 | 0.00 | 4.97 | 3.83 | 1.28 |
| 3 | Zinc Fluoride | 5.0 | 300 | 7.60 | 1.12 | 2.32 | 0.00 | 2.48 | 0.00 |
| 4 | Cobalt Fluoride | 5.0 | 300 | 4.75 | 2.75 | 6.10 | 7.55 | 3.50 | 7.75 |
| 5 | Zinc Chloride | 5.0 | 300 | 11.82 | 6.06 | 0.00 | 0.00 | 4.68 | 3.24 |

[a]All numbers refer to weight percent of individual components in the product mixture on a feedstock-free basis.
PIP — Piperazine
TEDA — Triethylenediamine
DETA — Diethylenetriamine
AEP — Aminoethylpiperazine
TAEA — Tris(aminoethyl)amine
TETA — Triethylenetetramine
BAEP — N,N'—Bis(aminoethyl)piperazine
PEEDA — N—(Piperazinoethyl)ethylenediamine
AE-TETA — N—(Aminoethyl)triethylenetetramine
TEPA — Tetraethylenepentamine
AE-BAEP — N—(2-(2-aminoethylamino)ethyl)-N'—(2-aminoethyl)piperazine
AE-PEEDA — N—(2-Piperazinoethyl)diethylenetriamine

TABLE 2

COMPARISON OF LEWIS ACID HALIDE AND PHOSPHORUS CATALYSTS

| Example | Catalysts | Level[a] | Conversion[b] | Selectivity[c] |
|---|---|---|---|---|
| 1 | Aluminum Chloride | 2.5 | 42.0 | 12.6 |
| 2 | Tin(IV) Chloride | 2.5 | 88.2 | 19.6 |
| 3 | Zinc Fluoride | 5.0 | 87.4 | 36.3 |
| 4 | Cobalt Fluoride | 5.0 | 93.9 | 28.9 |
| 5 | Zinc Chloride | 5.0 | 78.9 | 28.6 |
| 6 | Boron Phosphate | 5.0 | 94.9 | 31.0 |

[a]Mole percent of catalyst included, based on total amine feed.
[b]Weight percent of ethylenediamine and ethanolamine consumed in the reaction.
[c]Weight percent of noncyclic polyethylene amine products formed, based on total reaction product.

Tables 1 and 2 show that the Lewis acid halide catalysts were effective in producing a variety of linear and branched polyethylene polyamines. Tin (IV) chloride (2.5 mole %), zinc fluoride (5.0 mole %) and cobalt fluoride (5.0 mole %) gave particularly good conversion. As compared to the prior art catalyst, boron phosphate (5.0 mole %), selectivity was better with the zinc fluoride (5.0 mole %) catalyst. In general, although conversions were not as high as with boron phosphate, conversions were good. Only aluminum chloride (2.5 mole %) and tin (IV) chloride (2.5 mole %) did not afford selectivity which was about as good as, or better than the boron phosphate (5.0 mole %) run. It should be noted that the level of aluminum chloride and tin (IV) chloride was one-half that of boron phosphate.

EXAMPLES 7-11

A series of runs 7-11 were made to produce linear polyethylene polyamines by the reaction of ethylenediamine and monoethanolamine in a mole ratio of 2:1 by weight in the presence of Lewis acid halide catalysts. The reaction was carried out in a two milliliter shaker reactor under autogenous pressure at a temperature of 300° C. Each reaction was carried out for about two hours. At the completion of the reaction, the contents were cooled and the reaction mixture analyzed by gas liquid chromatography.

Tables 3 and 4 show results in terms of the amount of polyamines produced by the reactions. Conversion and selectivity are specified. The catalytic component was varied on the basis of weight mole percent of the total feed of ethylenediamine and monoethanolamine as indicated and was evaluated on the basis of its performance.

EXAMPLE 12

This run, which attempted to duplicate the art in terms of the catalyst taught by U.S. Pat. No. 4,036,881 for comparative purposes, was performed according to the procedure of Example 7 of this disclosure with the inclusion of boron phosphate (33 mg; 5.0 mole percent, based on the total amine feed) in place of tin (IV) chloride as catalyst for copolymerization of ethylenediamine and monoethanolamine which are present in a mole ratio of 2:1. Upon completion of the reaction, the contents of the reactor were cooled and the reaction mixture analyzed by gas liquid chromatography.

TABLE 3

POLYETHYLENE AMINES FROM ETHYLENEDIAMINE AND MONOETHANOLAMINE[a]

| RUN | CATALYST | LEVEL MOLE % | TEMP. °C. | PIP | TEDA | DETA | AEP | TAEA | TETA |
|---|---|---|---|---|---|---|---|---|---|
| 7 | Tin(IV) Chloride | 2.5 | 300 | 1.26 | 0.90 | 3.24 | 6.48 | 19.08 | 20.88 |

TABLE 3-continued

POLYETHYLENE AMINES FROM ETHYLENEDIAMINE AND MONOETHANOLAMINE[a]

| | | | | | | | | |
|---|---|---|---|---|---|---|---|---|
| 8 | Zinc Fluoride | 5.0 | 300 | 6.88 | 3.20 | 4.46 | 15.66 | 1.98 | 15.48 |
| 9 | Zinc Chloride | 5.0 | 300 | 5.37 | 0.51 | 2.40 | 6.75 | 6.96 | 1.59 |
| 10 | Aluminum Chloride | 2.5 | 300 | 22.32 | 6.36 | 2.64 | 17.40 | 1.08 | 1.50 |
| 11 | Cobalt Fluoride | 5.0 | 300 | 20.79 | 0.74 | 2.48 | 12.50 | 2.70 | 3.74 |

| RUN | CATALYST | LEVEL MOLE % | TEMP. °C. | BAEP | PEEDA | AE-TETA | TEPA | AE-BAEP | AE-PEEDA |
|---|---|---|---|---|---|---|---|---|---|
| 7 | Tin(IV) Chloride | 2.5 | 300 | 0.00 | 7.11 | 0.00 | 0.00 | 1.53 | 0.00 |
| 8 | Zinc Fluoride | 5.0 | 300 | 5.04 | 0.00 | 2.25 | 10.89 | 1.35 | 3.28 |
| 9 | Zinc Chloride | 5.0 | 300 | 6.03 | 15.42 | 0.00 | 12.90 | 0.00 | 8.52 |
| 10 | Aluminum Chloride | 2.5 | 300 | 4.26 | 3.06 | 0.00 | 4.92 | 1.20 | 1.32 |
| 11 | Cobalt Fluoride | 5.0 | 300 | 6.82 | 10.08 | 2.10 | 0.94 | 1.75 | 2.28 |

[a]All numbers refer to weight percent of individual components in the product mixture on a feedstock-free basis.
PIP — Piperazine
TEDA — Triethylenediamine
DETA — Diethylenetriamine
AEP — Aminoethylpiperazine
TAEA — Tris(aminoethyl)amine
TETA — Triethylenetetramine
BAEP — N,N'—Bis(aminoethyl)piperazine
PEEDA — N—(Piperazinoethyl)ethylenediamine
AE-TETA — N—(Aminoethyl)triethylenetetramine
TEPA — Tetraethylenepentamine
AE-BAEP — N—(2-(2-aminoethylamino)ethyl)-N'—(2-aminoethyl)piperazine
AE-PEEDA — N—(2-Piperazinoethyl)diethylenetriamine

TABLE 4

COMPARISON OF LEWIS ACID HALIDE AND PHOSPHORUS CATALYSTS

| Example | Catalyst | Level[a] | Conversion[b] | Selectivity[c] |
|---|---|---|---|---|
| 7 | Tin(IV) Chloride | 2.5 | 99.4 | 71.4 |
| 8 | Zinc Fluoride | 5.0 | 87.8 | 49.8 |
| 9 | Zinc Chloride | 5.0 | 94.8 | 35.9 |
| 10 | Aluminum Chloride | 2.5 | 98.3 | 15.4 |
| 11 | Cobalt Fluoride | 5.0 | 99.1 | 17.9 |
| 12 | Boron Phosphate | 5.0 | 66.2 | 43.0 |

[a]Mole percent of catalyst included, based on total amine feed.
[b]Weight percent of ethylenediamine and monoethanolamine consumed in the reaction.
[c]Weight percent of noncyclic polyethyleneamine products formed, based on total reaction product.

Again, the tables show that the Lewis acid halide catalysts gave good yields of polyethylene polyamines and as compared to the prior art boron phosphate the conversions were much higher. Selectivity using zinc fluoride (5.0 mole %) and zinc chloride (5.0 mole %) was comparable to that achieved with the boron phosphate (5.0 mole %) while the selectivity of tin (IV) chloride (2.5 mole %) was higher. In fact, tin (IV) chloride (2.5 mole %) gave the highest conversion (99.4%) and the highest selectivity (71.4%). Interestingly, cobalt fluoride (5.0 mole %) which afforded a conversion of about 99.1% concomitantly gave a low selectivity.

As compared to the results in Tables 1 and 2 where the runs used an ethylenediamine:monoethanolamine ratio of 1:2, it can be seen that by changing the ratio to 2:1 conversion generally increased for the same Lewis acid catalyst, substantially for aluminum chloride (2.5 mole %) and remained the same for zinc fluoride (5.0 mole %). Conversion for boron phosphate (5.0 mole %) decreased. Selectivity increased dramatically for tin (IV) chloride (2.5 mole %). With the other Lewis acid halide catalysts, except aluminum chloride (2.5 mole %), selectivity decreased somewhat. Selectivity of boron phosphate (5.0 mole %) increased.

Selectivity would be expected to increase as compared to the runs of Examples 1-6 since the ethanolamine concentration is lower in Examples 7-12 and it cannot react with itself as readily to form cyclic product.

EXAMPLES 13-26

A series of runs 13-26 were made to produce linear polyethylene polyamines by the reaction of ethylenediamine and monoethanolamine in a mole ratio of 1:1 by weight in the presence of Lewis acid halide catalysts. The reaction was carried out in a two milliliter shaker reactor under autogenous pressure at a temperature of 300° C. Each reaction was carried out for about two hours. At the completion of reaction, the contents were cooled and the reaction mixture analyzed by gas liquid chromatography.

Tables 5 and 6 show results in terms of the amount of polyamines produced by the reactions. Conversion and selectivity are specified. The catalytic component was varied on the basis of weight mole percent of the total feed of ethylenediamine and monoethanolamine as indicated and was evaluated on the basis of its performance.

TABLE 5

POLYETHYLENE AMINES FROM ETHYLENEDIAMINE AND MONOETHANOLAMINE[a]

| RUN | CATALYST | MOLE % | TEMP. °C. | PIP | TEDA | DETA | AEP | TAEA | TETA |
|---|---|---|---|---|---|---|---|---|---|
| 13 | Aluminum Chloride | 0.60 | 300 | 9.16 | 0.20 | 16.30 | 10.10 | 0 | 3.14 |
| 14 | Aluminum Chloride | 1.25 | 300 | 10.42 | 0.82 | 0.24 | 14.11 | 0.44 | 0.46 |
| 15 | Tin(IV) Chloride | 0.60 | 300 | 11.10 | 1.28 | 0.68 | 14.00 | 0.92 | 2.16 |

TABLE 5-continued
POLYETHYLENE AMINES FROM ETHYLENEDIAMINE AND MONOETHANOLAMINE[a]

| | CATALYST | LEVEL MOLE % | TEMP. °C. | | | | | | |
|---|---|---|---|---|---|---|---|---|---|
| 16 | Tin(IV) Chloride | 1.25 | 300 | 6.47 | 0.90 | 1.01 | 15.12 | 0.60 | 1.76 |
| 17 | Zinc Fluoride | 1.25 | 300 | 7.52 | 1.93 | 2.75 | 12.26 | 0 | 8.64 |
| 18 | Zinc Fluoride | 2.50 | 300 | 13.10 | 3.70 | 4.30 | 6.91 | 4.10 | 10.01 |
| 19 | Cobalt Fluoride | 0.83 | 300 | 22.46 | 1.53 | 2.09 | 16.53 | 1.29 | 6.70 |
| 20 | Cobalt Fluoride | 2.50 | 300 | 0 | 1.05 | 0.95 | 7.10 | 4.90 | 7.85 |
| 21 | Zinc Chloride | 1.10 | 300 | 2.94 | 0.88 | 5.32 | 3.05 | 0 | 5.28 |
| 22 | Zinc Chloride | 2.50 | 300 | 0 | 1.26 | 3.29 | 14.16 | 3.88 | 9.27 |
| 23 | Magnesium Chloride | 0.42 | 300 | 7.17 | 0.29 | 13.42 | 8.59 | 0 | 4.30 |
| 24 | Magnesium Chloride | 1.25 | 300 | 11.60 | 4.32 | 2.20 | 12.46 | 6.42 | 0.72 |
| 25 | Beryllium Chloride | 2.0 | 300 | 15.16 | 1.12 | 5.48 | 14.90 | 0.40 | 1.18 |
| 26 | Iron(III) Chloride | 1.25 | 300 | 17.29 | 5.95 | 2.24 | 14.28 | 2.28 | 0 |

| RUN | CATALYST | LEVEL MOLE % | TEMP. °C. | BAEP | PEEDA | AE-TETA | TEPA | AE-BAEP | AE-PEEDA |
|---|---|---|---|---|---|---|---|---|---|
| 13 | Aluminum Chloride | 0.60 | 300 | 3.07 | 7.37 | 0 | 3.98 | 1.57 | 4.35 |
| 14 | Aluminum Chloride | 1.25 | 300 | 5.58 | 13.50 | 7.64 | 1.06 | 3.82 | 1.40 |
| 15 | Tin(IV) Chloride | 0.60 | 300 | 6.42 | 8.90 | 5.56 | 7.34 | 5.34 | 3.98 |
| 16 | Tin(IV) Chloride | 1.25 | 300 | 6.81 | 8.82 | 10.13 | 7.88 | 6.53 | 5.67 |
| 17 | Zinc Fluoride | 1.25 | 300 | 3.24 | 0.98 | 0.86 | 10.81 | 0 | 1.58 |
| 18 | Zinc Fluoride | 2.50 | 300 | 5.90 | 1.60 | 2.02 | 13.10 | 0 | 3.70 |
| 19 | Cobalt Fluoride | 0.83 | 300 | 5.02 | 4.78 | 1.43 | 6.31 | 0 | 1.43 |
| 20 | Cobalt Fluoride | 2.50 | 300 | 13.30 | 10.25 | 5.00 | 0 | 9.10 | 7.00 |
| 21 | Zinc Chloride | 1.10 | 300 | 3.75 | 2.99 | 3.92 | 9.67 | 4.29 | 9.55 |
| 22 | Zinc Chloride | 2.50 | 300 | 7.50 | 4.30 | 0 | 15.50 | 1.68 | 4.47 |
| 23 | Magnesium Chloride | 0.42 | 300 | 2.72 | 6.25 | 0.59 | 1.39 | 1.56 | 1.01 |
| 24 | Magnesium Chloride | 1.25 | 300 | 7.12 | 9.48 | 0 | 0 | 11.46 | 4.20 |
| 25 | Beryllium Chloride | 2.0 | 300 | 5.22 | 12.56 | 0 | 0.94 | 5.48 | 3.86 |
| 26 | Iron(III) Chloride | 1.25 | 300 | 4.48 | 5.04 | 15.19 | 4.97 | 2.73 | 3.08 |

[a]All numbers refer to weight percent of individual components in the product mixture on a feedstock-free basis.
PIP — Piperazine
TEDA — Triethylenediamine
DETA — Diethylenetriamine
AEP — Aminoethylpiperazine
TAEA — Tris(aminoethyl)amine
TETA — Triethylenetetramine
BAEP — N,N'—Bis(aminoethyl)piperazine
PEEDA — N—(Piperazinoethyl)ethylenediamine
AE-TETA — N—(Aminoethyl)triethylenetetramine
TEPA — Tetraethylenepentamine
AE-BAEP — N—(2-(2-aminoethylamino)ethyl)-N'—(2-aminoethyl)piperazine
AE-PEEDA — N—(2-Piperazinoethyl)diethylenetriamine

EXAMPLE 27

This run, which attempted to duplicate the art in terms of the catalyst taught by U.S. Pat. No. 4,036,881 for comparative purposes, was performed according to the procedure of Example 13 of this disclosure with the inclusion of boron phosphate (17.0 mg; 2.5 mole percent, based on total amine feed) in the place of aluminum chloride as catalyst for copolymerization of ethylenediamine and monoethanolamine which are present in a mole ratio of 1:1. Upon completion of the reaction, the contents of the reactor were cooled and the reaction mixture analyzed by gas liquid chromatography.

TABLE 6
COMPARISON OF LEWIS ACID HALIDE AND PHOSPHORUS CATALYSTS

| Example | Catalyst | Level[a] | Conversion[b] | Selectivity[c] |
|---|---|---|---|---|
| 13 | Aluminum Chloride | 0.60 | 58.6 | 39.5 |
| 14 | Aluminum Chloride | 1.25 | 77.5 | 4.2 |
| 15 | Tin(IV) Chloride | 0.60 | 87.8 | 24.7 |
| 16 | Tin(IV) Chloride | 1.25 | 93.4 | 29.8 |
| 17 | Zinc Fluoride | 1.25 | 42.9 | 45.6 |
| 18 | Zinc Fluoride | 2.50 | 90.1 | 49.0 |
| 19 | Cobalt Fluoride | 0.83 | 86.0 | 25.7 |
| 20 | Cobalt Fluoride | 2.50 | 99.9 | 28.1 |
| 21 | Zinc Chloride | 1.10 | 69.9 | 46.8 |
| 22 | Zinc Chloride | 2.50 | 94.8 | 49.0 |
| 23 | Magnesium Chloride | 0.42 | 47.5 | 41.7 |
| 24 | Magnesium Chloride | 1.25 | 99.2 | 13.3 |
| 25 | Beryllium Chloride | 2.0 | 78.1 | 12.0 |
| 26 | Iron(III) Chloride | 1.25 | 99.5 | 15.5 |
| 27 | Boron Phosphate | 2.50 | 76.9 | 45.0 |

[a]Mole percent of catalyst included, based on total amine feed.
[b]Weight percent of ethylenediamine and monoethanolamine consumed in the reaction.
[c]Weight percent of noncyclic polyethyleneamine products formed, based on total reaction product.

Once again, Tables 5 and 6 show that the Lewis acid halide catalysts gave good yields of polyethylene polyamines. Generally, as compared to the prior art boron phosphate the conversions were as good or better while the selectivity for the most part was comparable. Iron (III) chloride (1.25 mole %), magnesium chloride (1.25 mole %) and cobalt fluoride (2.5 mole %) gave conversions of greater than 99%. Aluminum chloride (1.25 mole %) was least effective for selectivity.

The use of Lewis acid halides as catalysts for copolymerization of ethylenediamine and monoethanolamine provides a low-cost alternative to the phosphorus-containing catalysts of the prior art. In addition, several embodiments of this invention afforded higher selectivity to the commercially valuable noncyclic polyethylene polyamine products than do the phosphorus-containing catalysts. Such embodiments use tin (IV) chloride, zinc fluoride and zinc chloride preferably with the molar ratio of ethylenediamine to monoethanolamine greater than 1:1.

STATEMENT OF INDUSTRIAL APPLICATION

The inventive process for selectively preparing noncyclic polyalkylene polyamine compounds is applicable to the preparation of linear and branched polyalkylene polyamines which may be used to coagulate or flocculate suspended solids from liquid solutions or slurries, i.e. accelerate the separation of suspended solids from the suspending liquid phase. Linear and branched polyalkylene polyamines are also used in plasticizers, accelerators and antioxidants for polymers, and as comonomers (with diesters or urea-formaldehyde resins) for production of adhesives, water-proof sealers and protective coatings. In particular, polyethylene polyamines are useful in corrosion inhibitors in coolant and lubricant formulations, preparation of anion exchange resins finishing agents for textiles, and acid gas scrubbing.

What is claimed is:

1. A process for preparing a noncyclic polyalkylene polyamine which comprises:

contacting an alkyleneamine compound having two primary amino groups of the general formula:

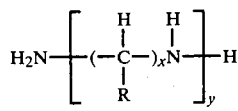

wherein R is hydrogen or a lower alkyl ($C_1$–$C_4$) radical, x is a number from 2 to about 6, and y is a number from 1 to about 4 with an alkanolamine compound having a primary or secondary hydroxyl group of the general formula:

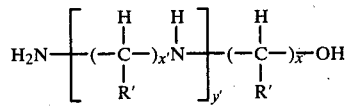

wherein R' is hydrogen or a lower alkyl ($C_1$–$C_4$) radical, x' is a number from 2 to about 6; and y' is a number from 0 to about 3;

the contacting being performed in the presence of an effective amount of a Lewis acid halide substance which is tin (IV) chloride, zinc chloride or zinc fluoride at a temperature sufficient to effect reaction between the alkyleneamine and the alkanolamine compounds under a pressure sufficient to maintain the reaction mixture essentially in liquid phase.

2. The process of claim 1 wherein the level of the Lewis acid halide substance is from about 0.01 to 10.0 mole percent based upon the total amount of alkylenediamine and alkanolamine present in the reaction mixture.

3. The process of claim 2 wherein the level of the Lewis acid halide substance is from about 0.05 to 5.0 mole percent based upon the total amount of alkylenediamine and alkanolamine present in the reaction mixture.

4. The process of claim 2 wherein the temperature is from about 200° C. to 350° C.

5. The process of claim 4 wherein the molar ratio of alkylenediamine to alkanolamine is from 1:10 to 10:1.

6. The process of claim 5 wherein the molar ratio of alkylenediamine to alkanolamine is from 1:5 to 5:1.

7. The process of claim 5 wherein the alkylenediamine is ethylenediamine and the alkanolamine is ethanolamine.

8. The process of claim 7 wherein the temperature is from about 250° to 300° C.

9. A process for preparing a linear polyalkylene polyamine which comprises:

contacting an alkyleneamine compound having two primary amino groups of the general formula:

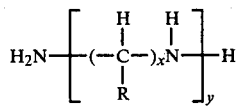

wherein R is hydrogen or methyl, x is a number from about 2 to 6, and y is a number from about 1 to 4 with an alkanolamine compound having a primary or secondary hydroxyl group of the general formula:

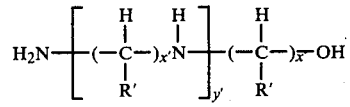

wherein R' is hydrogen or methyl, x' is a number from about 2 to 6, and y' is a number from about 0 to 3, and the molar ratio of alkylenediamine to alkanolamine is at least 1:1;

the contact being performed in the presence of about 0.01 to 10.0 mole percent, based on the total amount of alkylenediamine and alkanolamine present in the reaction mixture, of a Lewis acid halide substance which is tin (IV) chloride, zinc fluoride or zinc chloride at a temperature from about 200° to 350° C. under a pressure sufficient to maintain the reaction mixture essentially in liquid phase.

10. The invention of claim 9 wherein the catalyst is tin (IV) chloride and the alkylenediamine:alkanolamine molar ratio is about 2:1.

* * * * *